(12) United States Patent
Knauer (10) Patent No.: US 7,886,744 B2
(45) Date of Patent: Feb. 15, 2011

(54) TUBE-FORMED EARPLUG WITH INTEGRAL STEM

(75) Inventor: Richard Knauer, Carmel, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 116 days.

(21) Appl. No.: 11/545,629

(22) Filed: Oct. 10, 2006

(65) Prior Publication Data

US 2007/0089755 A1    Apr. 26, 2007

Related U.S. Application Data

(60) Provisional application No. 60/725,569, filed on Oct. 10, 2005.

(51) Int. Cl.
*A61F 11/00* (2006.01)
*H04R 25/00* (2006.01)
*H04R 25/02* (2006.01)
*A61B 7/02* (2006.01)

(52) U.S. Cl. .............. 128/864; 128/867; 181/129; 181/130; 181/134; 181/135

(58) Field of Classification Search ............. 128/864, 128/866, 865, 867; 2/209; 181/130, 134, 181/135, 129; 381/322; D24/106; 264/464, 264/477, 148, 150, 176.1, 177.1, 177.14
See application file for complete search history.

(56) References Cited

U.S. PATENT DOCUMENTS

| | | | | |
|---|---|---|---|---|
| 5,573,015 | A * | 11/1996 | Williams | 128/864 |
| 7,096,872 | B2 * | 8/2006 | Ligon et al. | 128/864 |
| 2003/0029458 | A1 * | 2/2003 | Tlemens | 128/864 |
| 2007/0221232 | A1 * | 9/2007 | Jenkins | 128/864 |

FOREIGN PATENT DOCUMENTS

| | | |
|---|---|---|
| CH | 287 384 | 11/1952 |
| CH | 287384 A | 11/1952 |
| WO | WO 2004/028777 | 4/2004 |
| WO | WO 2004/028777 A1 | 4/2004 |

OTHER PUBLICATIONS

International Search Report; PCT/US2006/039643; Jan. 4, 2007.

* cited by examiner

*Primary Examiner*—Patricia M Bianco
*Assistant Examiner*—Ophelia Hawthorne
(74) *Attorney, Agent, or Firm*—Karl C. Hanson (57) ABSTRACT

An earplug and a method of manufacturing the earplug are provided, the earplug including a sound attenuating element and a stem where the sound attenuating element includes a flange which extends rearwardly over a portion of the stem, and where the sound attenuating element and the stem are integrally formed of a resilient compressible material.

15 Claims, 4 Drawing Sheets

TUBE-FORMED EARPLUG WITH INTEGRAL STEM

CROSS-REFERENCE TO RELATED APPLICATION

This application is related to and claims the benefit of U.S. Provisional Patent Application Ser. No. 60/725,569 filed on 10 Oct. 2005, the entire contents of which are herein incorporated by reference.

TECHNICAL FIELD OF INVENTION

The invention concerns hearing protection devices and, more particularly, an extruded earplug having an integrally formed sound attenuating element and a stem.

BACKGROUND OF INVENTION

The use of hearing protective and noise attenuating devices is well known, and various types of devices are available including, but not limited to, ear muffs, semi-aural devices, and earplugs. Earplugs are often preferred for their effectiveness in attenuating sound and for comfort properties provided thereby.

An earplug generally comprises a sound attenuating element which is placed in the ear canal of a wearer to provide a desired sound attenuation. The sound attenuating element is commonly made of a resiliently compressible, full recovery material such as a foam or a rubber.

The earplug may further include a rigid or semi-rigid stem embedded partly or entirely in the resilient sound attenuating element. The stem provides a degree of rigidity to the earplug which enables the earplug to be easily inserted and pushed into the ear canal of a user. Further, where the stem extends from the sound attenuating element, it may serve as a handle of the earplug to facilitate insertion and removal of the earplug.

Commonly, resilient sound attenuating elements for earplugs are formed by molding techniques which utilize a specific mold to shape the sound attenuating element. For example, the resilient material in liquid form is injected into the mold and allowed to set therein. Once the material is solidified, the sound attenuating element is ejected from the mold.

If the earplug includes a stem, such is manufactured separately from the sound attenuating element. For example, the stem may be produced in a separate molding process. Once completed, the stem may be adhered adhesively to the sound attenuating element. Alternatively, the completed stem may be placed into the mold of the sound attenuating element when the resilient material is in the liquid form. In this way, the resilient material may cure around and bond onto the stem.

This multi-step molding and assembly procedure for forming stemmed foam earplugs is often inconvenient and cumbersome. For example, if a manufacturer desires several differently shaped and/or sized earplugs, he or she must produce and maintain an equivalently corresponding number of molds. Further, the material used to form the sound attenuating element may stick to the mold during the solidification process and thus tear or otherwise deform upon ejection. Also, sound attenuating elements cast in a mold as described may include seam lines from the mold and also necessarily include any imperfections on the molding surface of the mold. Further, the additional steps of manufacturing the stem and of affixing the stem to the sound attenuating element are often regarded as time consuming and costly.

Thus, a stemmed earplug is desired where the sound attenuating element and the stem may be produced conveniently, rapidly, and at reduced cost while still maintaining a high production quality.

BRIEF SUMMARY OF THE INVENTION

The above discussed and other problems and deficiencies of the prior art are overcome or alleviated by the invention which provides a novel and nonobvious hearing protection device.

The invention provides, in one illustrative example, a unique earplug including a sound attenuating element and a stem where the sound attenuating element includes a flange which extends rearwardly over a portion of the stem, and where the sound attenuating element and the stem are integrally formed of a resilient compressible material.

The invention also provides a unique method of manufacturing an earplug. In one embodiment, the invention provides a method of manufacturing an earplug, including forming a hollow tube of a resilient compressible material, permanently deforming the tube to form a closed solid portion, allowing an open portion of the hollow tube to remain adjacent to the closed portion, and pivoting the open portion outwardly and over the closed portion to delimit a sound attenuating element and a stem.

In another embodiment, the invention provides a method of forming a plurality of earplug precursors where the method includes extruding a hollow tube of a foam material from an extruding die, shaping the extruded hollow tube to include alternating closed solid portions and open hollow portions, and at least partially severing the shaped extruded tube at the closed solid portions and at the open hollow portions.

The above-discussed and other features and advantages of the apparatus and method of the invention will be appreciated and understood by those skilled in the art from the following drawings and detailed description.

BRIEF DESCRIPTION OF THE FIGURES

Referring now to the drawings wherein like elements are numbered alike in the several FIGURES.

DETAILED DESCRIPTION OF THE PREFERED EMBODIMENT

Figure 1:
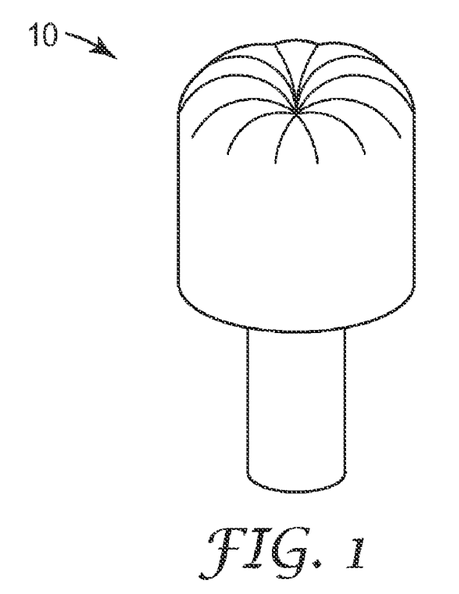
FIG. 1 is a top perspective view of an earplug in one embodiment of the invention.
Figure 2:
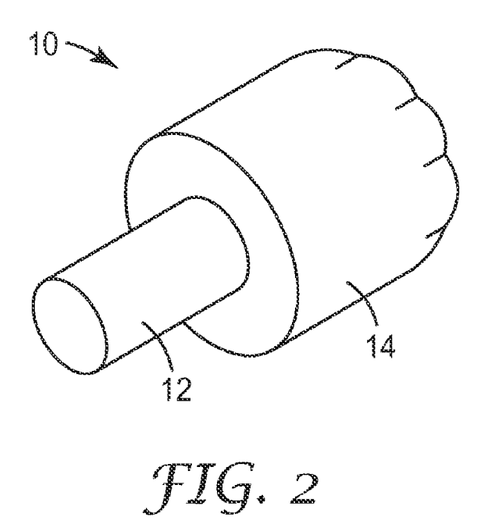
FIG. 2 is a bottom perspective view thereof.

FIGS. 1 and 2 show an earplug 10 in one embodiment of the invention. The earplug 10 generally comprises a stem 12 and a sound attenuating element 14. As will be discussed further herein in detail, the stem 12 and the sound attenuating element 14 are formed integrally together of a resilient foam material. The stem 12 is used to handle the earplug 10 and, particularly, to insert the sound attenuating element 14 into the ear canal of a user and to remove the element 14 therefrom. The sound attenuating element 14 is sized and shaped to be received and retained within the ear canal. That is, the sound attenuating element 14 includes a diameter slightly larger than a diameter of an average ear canal such that, upon insertion, the element 14 compresses slightly into a friction fit within the ear canal. The stem 12 is sized and shape to protrude slightly from the ear canal when the earplug is worn. In this way, the stem 12 may serve as a handle for adjusting the position of the earplug 10 or for removing the earplug 10.

Figure 3:
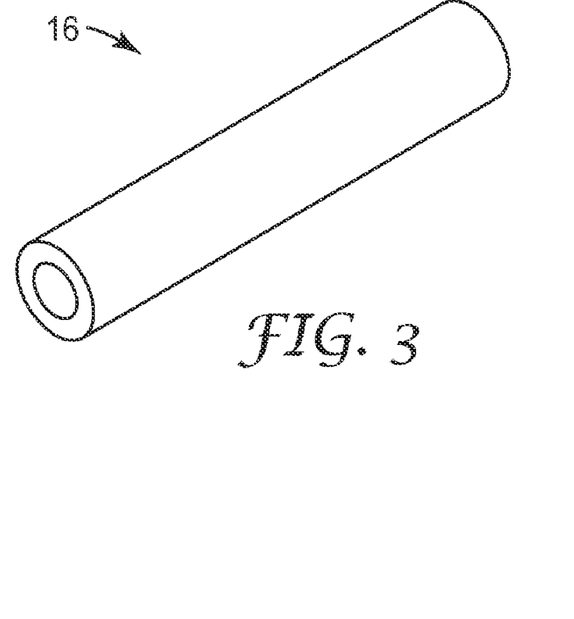
FIG. 3 is a perspective view of a tube used in form the earplug of FIG. 1.
Figure 4:
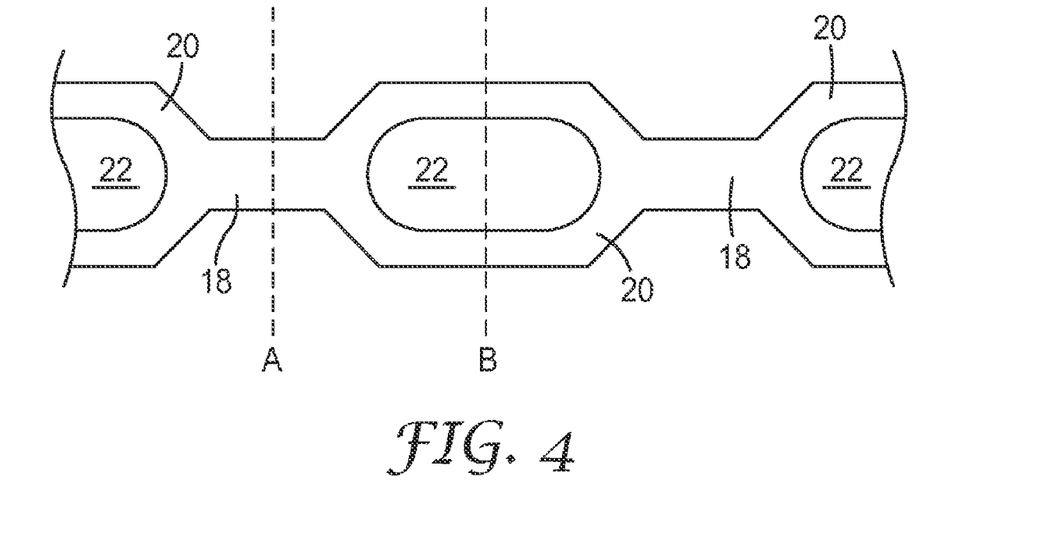
FIG. 4 is a partial cross-sectional view of tube of FIG. 3 after a shaping procedure.

The earplug 10 is formed by a unique process which first involves the formation of a tube 16, as shown in FIG. 3. The tube 16 is simply a hollow elongated cylindrical body, preferably made of foam and more preferably extruded foam. The tube 16 may be of any length desired and generally is a multiple of the length of the earplugs to be formed therefrom, as will be discussed in greater detail herein. Next, the tube 16 is pinched closed at regular intervals across the longitudinal length of the tube 16. This forms alternating closed portions 18 and open portions 20, as shown in FIG. 4. The closed portions 18 constitute permanently deformed areas of the tube 16 which are solid and include no significant hollow space remaining therein. The open portions 20, on the other hand essentially represent areas of the tube 16 which were not pinched closed. These open portions 20 retain the same general size and shape of the original tube 16. Resultantly, each open portion 20 delimits a space 22 at an interior thereof.

As will be discussed in further detail herein, the closed portions 18 of the tube are densified during formation thereof. That is, during the compression of the tube 16, air entrained within the foam is forced out of the tube 16. This results in a densification of the foam which forms the closed portions 18. Thus, the foam material of the closed portions 18 has a greater density than the foam of the open portions 20.

Figure 5:
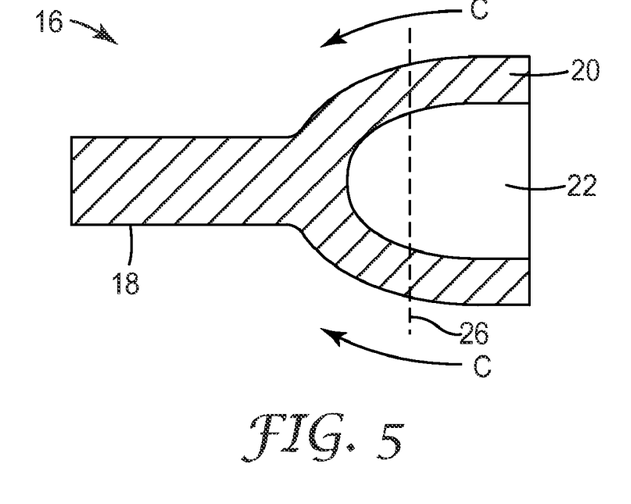
FIG. 5 is a cross-sectional view of an earplug precursor.
Figure 6:
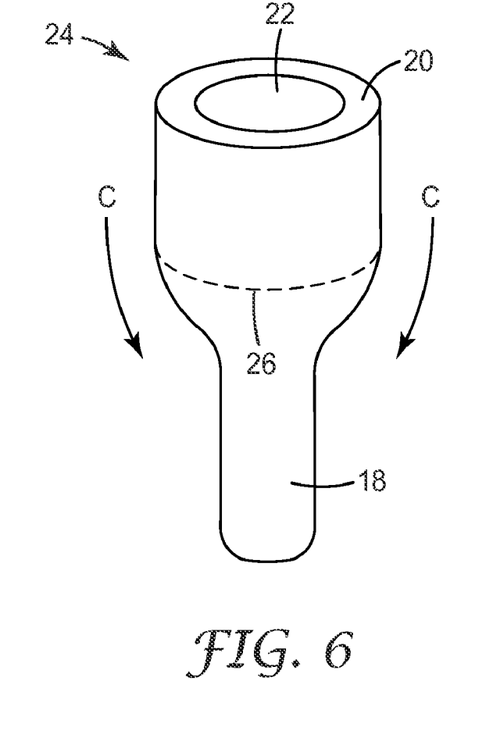
FIG. 6 is a perspective view thereof.

The next step in forming the earplug 10 involves severing the tube 16. The tube 16 is cut at both the closed portion 18 and the open portion 20. Particularly, the closed portion 18 is severed at approximately a line A shown in FIG. 4. The open portion is severed at approximately a line B of FIG. 4. The lines A and B are generally perpendicular to a longitudinal axis of the tube 16. This severing of the shaped tube 16 forms an earplug precursor 24 as shown in FIGS. 5 and 6. The earplug precursor 24 includes part of the closed portion 18, part of the open portion 20, and part of the space 22 delimited therein. For example, the cutting line A may bisect the closed portion 18 of FIG. 4. Thus, the earplug precursor 24 includes approximately one-half of the closed portion 18. Similarly, the cutting line B may bisect the open portion 20 of FIG. 4 and thus the earplug precursor 24 retains approximately one half of the open portion 20. In this way multiple earplug precursors 24 are made from one tube 16. Of course, the location of the cutting lines A and B may be varied to change the relative sizes and dimensions of adjacent earplug precursors 24 formed from the tube 16.

Referring to FIGS. 5 and 6, the earplug precursor 24 includes a hinge point 26 indicated illustratively by a dashed line. This hinge point 26 extends around a circumference of the open portion 20 of the earplug precursor 24. Because the tube 16 is originally extruded of a resilient, compressible foam material, the open portion 20 of the earplug precursor 24 is capable of hinging at the hinge point 26 outwardly and rearwardly toward the closed portion 18, as indicated by arrows C. That is, the open portion 20 may be flipped backward approximately at the hinge point 26 toward and over the closed portion 18. Once this movement of the open portion 20 is made, the earplug precursor 24 assumes the configuration of the earplug 10 shown in FIGS. 1 and 2. The flipped back open portion 20 forms the sound attenuating element 14. The closed portion 18 assumes the role and function of the stem 12.

The precise location of the hinge point 26 upon the open portion 20 depends mainly upon the ductility of the material used to form the tube 16. A more ductile material will tend to result in a hinge point 26 closer toward the closed portion 18. A material of less ductility will tend to hinge toward an area further from the closed portion 18.

Figure 7:
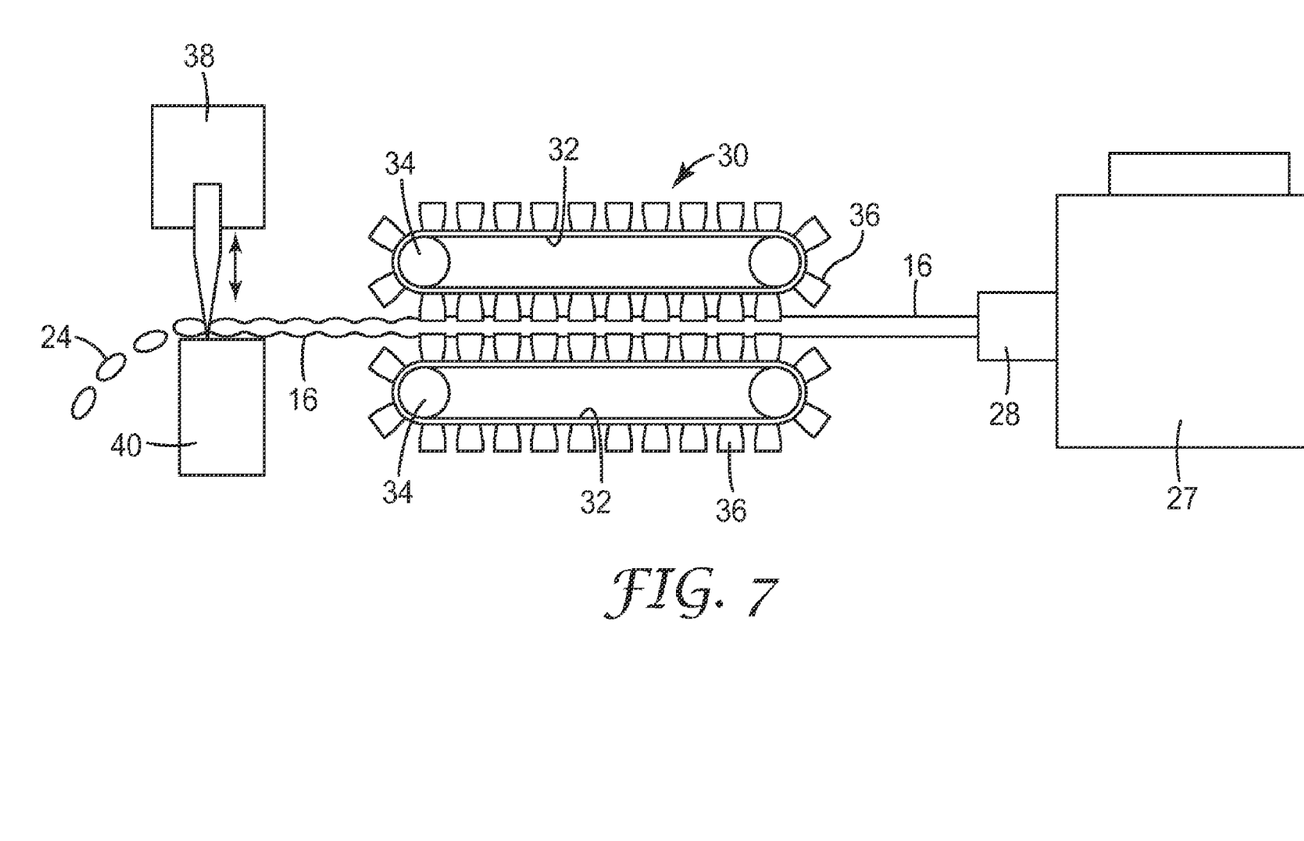
FIG. 7 is a schematic view of an in-line process for forming an earplug in one embodiment of the invention.

The earplug precursor 24 is preferably formed by an in-line extrusion/shaping/cutting process, as represented schematically in FIG. 7. The material used for forming the tube 16 is introduced into an extruder 27 where the material is mixed and treated as necessary in preparation for extrusion. Then material is extruded through a die 28 to form the tube 16. Preferably, upon exiting the die 28 of the extruder 27, the tube 16 will be a substantially completely foamed material, although it may only be partially foamed. After exiting the die 28, the tube 16 is shaped as desired.

The step of shaping may be done in any suitable manner. For example, it is possible to utilize opposing surfaces, one or both of which are shaped to a desired configuration, where the surfaces contact the tube 16 for plastically deforming the tube 16 (e.g., while the temperature of the tube 16 is still at or near the melting point of the extruded material). In a preferred embodiment, shaping is performed nearly simultaneously about substantially the entirety of the periphery of the tube 16. A particularly preferred approach to shaping is by deformation of the tube 16 in accordance with a suitable method, such as those disclosed in U.S. Pat. Nos. 4,789,322; 4,504,206; and 3,981,663; and U.S. Application Publication 2005/0060567; hereby expressly incorporated by reference. Preferably, a shaping machine 30 will have a line speed of at least about 1 meter per minute, more preferably at least about 5 meters/minute, and still more preferably at least about 12 meters/minute and even still more preferably at least about 20 meters/minute. In this manner, it is contemplated to produce the earplug precursors 24 in an amount ranging from about 5 to about 30 kg/hour or higher, and more preferably about 15 to about 25 kg/hour.

In general, as seen for example in FIG. 7, it is contemplated that a suitable shaping machine 30 will include opposing webs 32, chains or the like that rotate about a sprocket or other suitable roller 34 and which each include a plurality of successive traveling mold portions 36 (which optionally may be heated, removable, interchangeable with other mold portions, or contain a sharp edge for cutting). Upon placing tube 16 between the mold portions 36 (e.g., aligning the tube 16 with a suitable guide device or in a channel disposed between the mold portions 36) the webs 32 are synchronously advanced for feeding the tube 16 through the opposing mold portions 36, whereupon the tube 16 is shaped to the desired shape (corresponding to the shape of the mold portions). That is, the closed portions 18 and the open portions 20 are formed in the tube 16 by the opposing mold portions 36. More particularly, two oppositely disposed mold portions 36 engage the tube 16 at opposite sides thereof and act to compress or pinch the tube 16 inward toward its center. Since the tube 16 is freshly extruded and still warm, this compression permanently deforms the tube 16 to form the closed portions 18 and thus delimit the open portions 20.

The shaping machine 30 may be located immediately adjacent the extrusion die 28 or spaced apart therefrom. Thus, it is possible that some foaming may occur during shaping. In this manner, it is possible that the temperature of the extruded tube 16 may be controlled during the shaping thereof by heating or cooling the tube 16 along the line. Other similar continuously fed shaping machines and techniques may also be employed and the present invention is therefore not limited solely to the above embodiment. For example, rather than using opposing traveling mold portions, the extruded tube 16 may be shaped by a stationary stamp arrangement where the tube 16 is passed beneath a stamp which is selectively lowered upon the tube 16 to form the closed portion 18 and then raised to allow passage of the tube 16. Alternatively, a variable extruding die 28 may be employed such that the tube 16 is extruded from the extruder 27 in the shaped form as shown in FIG. 4. That is, the extruding die 28 may be configured to pass the tube 16 as including the alternating closed and open portions 18 and 20. In this alternate arrangement, clearly no shaping of the tube 16 would be required. Thus, the extruded shaped tube 16 would simply be passed directly to the cutter 36.

The opposing mold portions 36 may be fitted with suitable vacuum lines for aid in forming the earplugs 10, fluid lines (e.g., air or water) for temperature control of the tube 16 as it is being shaped, or a combination thereof. It will further be appreciated that controlled cooling of the extruded tube 16 could have the effect of forming a skin thereon, which in turn, could help impart a certain rigidity and strength to the resulting earplug precursors 24.

As discussed, any of a plurality of techniques may be employed to shape the tube 16 so as to include the closed portions 18 and the open portions 20. As mentioned, the tube 16 is preferably formed of a foam. Importantly, the applied shaping technique must be sufficient to densify the portions of the tube 16 which are formed into the closed portions 18. Namely, these portions 18 must be sufficiently compressed not only to pinch closed the respective areas of the tube 16 but also to expel air entrained within the foam itself. This air expulsion increases the density of the foam in the areas of closed portions 18 relative to the density of the foam at the open portions 20. This increase in density provides an added degree of rigidity to the closed portions 18. This densificaiton rigidity provides numerous advantages to the resulting earplug 10, as will be discussed further herein.

After shaping the tube 16 to include the open and closed portions 18 and 20, the tube is passed to a cutter 38 located downstream of the shaping machine 30. As mentioned above, the shaped tube 16 is severed at or about the cutting lines A and B to thus form the earplug precursors 24. The cutter 38 may simply comprise a blade which descends to cut the shaped tube 16 against a cutting block 40, as shown in FIG. 7. Alternatively, the cutter 38 may comprise two or more oppositely disposed cutting blades which move relative to one another to selectively sever the shaped tube 16. Further still, the cutter may be incorporated into the shaping machine 30, for example, the opposing mold portions 36 may include a cutting element such that the tube 16 is shaped and severed in one process step.

Other processing steps may also be employed as desired. For example, during extrusion, during shaping or both, the extruded tube 16 or earplug precursors 24 may be stretched, cut with a hot blade, or both for forming a skin on one or both ends of the resulting earplug 10. Examples of suitable stretch-cutting techniques that may be employed are disclosed in U.S. Pat. Nos. 4,708,624 and 4,617,849, hereby incorporated by reference. Thus, the extruded tube 16 or earplug precursors 24 may be stretched longitudinally and cut transversely while stretched. It is also possible that flash will be generated during processing, and the present invention also contemplates that a step be employed for flash removal, in instances when control over processing and equipment cannot avoid the formation of flash in the first instance.

Additionally, the in-line process of forming the earplug 10 described herein is provided by way of example only. That is, the process need not be an in-line process. The tube 16 may first be extruded and then separately shaped and severed, as desired. The un-shaped tube 16 may be stored or shipped and then later heated and shaped into the configuration of FIG. 4. When desired, the shaped tube 16 may be severed. The manufacturing process of the earplug 10 may further be varied as desired.

The outer surface of an earplug 10 in accordance with the present invention may exhibit any suitable surface texture, contour or combination thereof. The earplug 10 may include a smooth surface as illustrated in the above embodiments. Alternatively, the earplug 10 may include a corrugated outer surface or other surface features as desired. Additionally and/or alternatively, the in-line formation of the earplug 10 may further include a printing and/or color stage where print and/or color is applied to a portion or to an entirety of the earplug precursor 24. The extruded tube 16 or earplug precursors 24 may be coated over some or all of their bodies with a suitable coating, such as a tackifier, a powder, a reduced friction material, a medicament (e.g., a fungicide, a bactericide, or another medicine), an antiseptic, or combinations thereof. The earplugs 10 are preferably at least about 25 mm in length. However, smaller or larger earplugs 10 may be made according to the invention.

As mentioned, during formation of the earplug precursor 24 of FIGS. 5 and 6, the closed portion undergoes a densification process by which air entrained in the foam is expelled therefrom. The resulting closed portion 18 has a greater density than the open portion 20. This greater density imparts a greater rigidity to the close portion 18. This is particularly advantageous because, as discussed, the closed portion 18 forms the stem 12 of the earplug 10 when the open portion 20 is hinged backward into the sound attenuating position. The enhanced stiffness of the closed portion 18 facilitates the rotation of the open portion 20 about the hinge point 26. That is, the closed portion 18 yields and deflects in a lesser amount than the open portion 20 during the hinging process. In this way, the closed portion 18 acts as a stop which encourages the hinging of the open portion 20. Additionally, the enhanced stiffness of the resulting stem 12 is highly beneficial in handling, inserting, and removing the earplug 10. for example, the rigidity of the stem 12 enables the wearer to push the sound attenuating element 14 into engagement within the ear canal.

The earplug 10 is configured to provide a mean attenuation level of at least about 10 dB, and more preferably at least about 20 dB within a frequency range of about 125 to about 250 Hz; and at least about 20 db, and more preferably at least about 35 db for frequencies greater than about 500 Hz. A highly preferred earplug 10 in accordance with the present invention is believed to exhibit an attenuation level of at least about 40 db at a frequency of about 3000 Hz. Thus, preferred earplugs 10 in accordance with the present invention are believed to and preferably will exhibit a Noise Reduction Rating (NRR) of at least about 5, more preferably at least about 15, and still more preferably at least about 20; and in one preferred embodiment, the earplugs may have a NRR of between about 15 and 40, and more preferably between about 20 and 30.

The material used to form the earplug 10 preferably has a density in a range from about 12 to 31 pcf (about 0.2 to 0.5 g/cc), or more preferably, within a range of from about 20 to 25 pcf (about 0.3 to 0.4 g/cc). In addition, in one preferred embodiment, the material of the earplug 10 (in an unfoamed state) would exhibit a Shore A durometer hardness of between about 50 and about 80.

Foamed materials discussed herein may be of an open or closed cell material. In one preferred embodiment, at least about 50% by volume, more preferably at least about 65% by volume of the overall cell volume will include closed cells. The foamed materials of the earplugs 10 may be skinned or unskinned. They may have a continuous or uniform density throughout, or a density gradient. Preferably the material employed will be sufficiently pliable and elastic that a user will be able to hinge the precursor 24 into the earplug 10 configuration. The material shall be sufficiently compressible in order to compress the earplug 10 for insertion into an ear. The material shall further be sufficiently resilient such that the earplug 10 once inserted with expand so as to retain the earplug 10 within the ear. Thus, generally it will be appreciated that the material of the earplug with exhibit a relatively low compression set and a relatively low load/deflection.

Preferred materials for forming the earplug 10 are low density thermoplastic elastomeric materials such as thermoplastic polyolefins/ethylene-propylene (PEP OR EPDM), thermoplastic block copolymers/styrene-butadiene (SBS) and styrene-isoprene (SIS), thermoplastic polyester, thermoplastic polyurethane (PU)/polyester/polyether, thermoplastic vulcanizates (e.g., comprising blends of cured olefin rubber and thermoplastic olefin resin), poly (vinyl ester) (e.g., chemically blown), melt processible rubbers, polyamide blocks, thermoplastic rubber, viscoelastic polyurethane, and polyvinyl chloride (PVC). Santoprene.RTM. thermoplastic rubber may also be used. Other thermoplastic foams may alternatively be employed. Blends of the above materials likewise may be employed.

In one embodiment where a low friction surface is desired, the earplug 10 is coated over at least a portion of their external surfaces with a low friction coating, which may take the form of a powder, wax, an oil, or even a polymer (such as a fluoropolymer, a high-density polyolefin (e.g., HDPE), a silicon-containing compound (e.g., an organosilane) or the like. The coating may be emulsified or dispersed in a liquid to facilitate the coating step. Alternatively, for example, when a polymer coating is employed it is possible that it is coextruded with the foamed thermoplastic. Other suitable coating techniques may be employed such as dipping, brushing, curtain coating, spraying, swabbing, or the like. Other organic or inorganic coatings may also be employed. Additives or reinforcements may also be incorporated into or on the surface of the earplug, such as colorants, stabilizers, fillers, or other art-disclosed additives.

The extruded tube 16 is described by way of example only as being completely severed by the cutter 36 to form the earplug precursors 24. In another embodiment of the invention, the tube 16 may be partially severed such that adjacent precursors 24 remain partly attached in a chain. In this way, the precursors 24 may be packaged, shipped, and handled as a chain and then be completely detached by the user prior to formation of the earplug 10 and insertion thereof into the earcanal. Alternatively, the open portions 20 of the shaped tube 16 may be fully cut while the closed portions 18 may be only partially severed thus resulting in pairs of precursors 24 partially attached at the closed portions 18. In this configuration, the end user may handle the precursors 24 as a paired unit and then, prior to use, completely sever the precursors 24 and hinge the open portions 20 to form two independent earplugs 10.

As alluded to herein, the end user may manually hinge the open portion 20 of the earplug precursor 24 about the hinge point 26 in order to form the earplug 10. The user then may insert the earplug 10 into the ear canal. Alternatively, the earplug 10 configuration may be attained manually or by machine prior to the end user 10 receiving the earplug 10. For example, the in-line process described above with reference to FIG. 7 may further include a hinging step where the precursors 24 are manually or mechanically manipulated into the configuration of the earplug 10. Then, the formed earplugs 10 may be distributed to the end user.

The earplug 10 may further include a cord attached to the stem 12 which extends to a second earplug 10 to provide a connected pair of earplugs 10. The cord may be affixed to the earplugs 10 by any conventional method, for example by adhesively bonding the cord to the stem 12 after formation of the earplugs 10.

In another embodiment of the invention, the closed portion 18 of the tube 16 may be formed to have a length significantly greater than a length of the open portion 20. In this embodiment, only the open portions 20 are severed, the closed portions 18 are not cut. The resulting assembly comprises to oppositely disposed open portions 20 and an elongated closed portion 18 extending therebetween. The open portions 20 may then be manually or mechanically hinged backward at the respective hinge points 26 to form earplugs 10 at either end of the elongated closed portion 18. Here, the closed portion 18 serves as a cord or a band extending between the earplugs 10. The respective earplugs 10 may be inserted into the ears of a user with the closed portion 18 extending beneath the chin of the user or behind the neck as is seen commonly with corded earplugs and banded semi-aural devices.

While the tube 16 is described herein as preferably being formed by extrusion, other manufacturing processes are contemplated by the broad scope of the invention. For example, the tube 16 may be molded by conventional means and then, prior to fully curing, may be shaped into the arrangement of FIG. 4 and then cut into the precursors 24 of FIGS. 5-6. Alternatively, the tube 16 may be molded directly into the arrangement of FIG. 4 and then cut into the precursors 24, thus avoiding a shaping step.

While the tube 16 and resulting earplugs 10 are described herein as being formed by a foamed material, other materials are contemplated by the invention. For example, the tube 16 may be formed of a plastic material, a rubber material, etc.

The material preferably utilized in forming the earplug 10 is sufficient for retaining the open portion 20 of the precursor 24 in the hinged position to thus maintain composition of the earplug 10. However, if desired an adhesive may be applied between the hinged open portion 20 and the closed portion to rigidly retain the open portion 20 thereon. Alternatively, the open portion 20 may be heat welded to the closed portion 18 or secured thereto by any other suitable known means.

Dimensions and materials identified in the attached Figures are for illustration purposes and may vary depending upon the intended application in accordance with the teachings of the present invention. The present invention is not intended to be limited to the specific features of the Figures even though the invention encompasses the same.

Thus, the invention provides an earplug having a stem and a sound attenuating element where the stem is made integrally of the same material as the sound attenuating element. Thus, no separate manufacture of the stem is required. Further, a separate step of affixing the stem to the sound attenuating elements is also not required. Thus, an earplug is provided which may be rapidly produced in large batches in a low-cost efficient manner while production quality and consistency are maintained at a desirably high level.

It will be apparent to those skilled in the art that, while exemplary embodiments have been shown and described, various modifications and variations can be made to the present apparatus and method disclosed herein without departing from the spirit or scope of the invention. Accordingly, it is to be understood that the various embodiments have been described by way of illustration and not limitation.

The invention claimed is:

1. An earplug, comprising:
a sound attenuating element; and
a stem that has a first end;
wherein the sound attenuating element comprises a flange that defines an opening at an end opposite the first end of said stem in a first configuration, said opening being open to an exterior of the earplug, and wherein said flange is extendable rearwardly over a portion of the stem in a second configuration; and
wherein the sound attenuating element and the stem are integrally formed of a resilient compressible material.

2. The earplug of claim 1, wherein the sound attenuating element is pivotal about a hinge point from a forwardly facing open position to the rearward position over the stem.

3. The earplug of claim 2, wherein the sound attenuating element comprises a single flange which delimits a hollow inner space in the forwardly facing open position.

4. The earplug of claim 1, wherein the resilient compressible material is an extruded foam material.

5. The earplug of claim 1, wherein the earplug comprises a portion of an extruded foam tube, the stem comprising a permanently closed portion of the tube and the sound attenuating element comprising an open portion of the tube, wherein the sound attenuating element is pivotal about a hinge point from a forwardly facing open position to the rearward position over the stem.

6. A method of manufacturing an earplug, comprising:
forming a hollow tube of a resilient compressible material;
permanently deforming the hollow tube to form a closed solid portion and open hollow portion;
at least partially severing the hollow tube at the closed solid portion and the open hollow portion to form a stem having a first end;
allowing an open portion of the hollow tube to be open to an exterior of the earplug opposite the first end of the stem via said severing at said open hollow portion;
allowing said open portion of the hollow tube to remain adjacent to the closed portion;
pivoting the open portion outwardly and over the closed portion to delimit a sound attenuating element and a stem.

7. The method of claim 6, further comprising permanently deforming the hollow tube to include a plurality of alternating closed and open portions.

8. The method of claim 7, further comprising at least partially severing the tube at the alternating closed and open portions to form a plurality of said earplugs.

9. The method of claim 6, wherein said forming the tube comprises extruding the tube of a foam material.

10. The method of claim 6, wherein said permanently deforming comprises compressing an area of the tube with opposing traveling mold portions to form said closed portion.

11. A method of forming a plurality of earplug precursors, comprising:
extruding a hollow tube of a foam material from an extruding die;
shaping the extruded hollow tube to include alternating closed solid portions and open hollow portions;
at least partially severing the shaped extruded tube at the closed solid portions and at the open hollow portions to form a stem portion having a first end and an open portion facing opposite the first end of the stem, respectively; and
causing the open portion to be flipped 180° over the stem portion such that the open portion no longer faces opposite the first end of the stem.

12. The method of claim 11, wherein said tube is completely severed at the closed solid portions and the open hollow portions to form said plurality of earplug precursors.

13. The method claim 12, further comprising hinging a remaining open hollow portion of each of the earplug precursors into a rearward position over the respective closed solid portion wherein the hinged open hollow portion forms a earplug sound attenuating element and wherein the closed solid portion forms a corresponding earplug stem.

14. The method of claim 11, wherein said shaping comprises compressing areas of the tube with opposing traveling mold portions to form said closed solid portions and to delimit said open hollow portions.

15. The method of claim 11, wherein said tube is completely severed at the open hollow portions and partially severed at the closed solid portions to form a plurality of pairs of attached earplug precursors.

* * * * *

UNITED STATES PATENT AND TRADEMARK OFFICE
CERTIFICATE OF CORRECTION

| | | |
|---|---|---|
| PATENT NO. | : 7,886,744 B2 | Page 1 of 1 |
| APPLICATION NO. | : 11/545629 | |
| DATED | : February 15, 2011 | |
| INVENTOR(S) | : Richard Knauer | |

It is certified that error appears in the above-identified patent and that said Letters Patent is hereby corrected as shown below:

<u>Cover page, (74) Attorney, Agent, or Firm</u>
Delete "C." and insert --G.-- therefore.

<u>Column 2</u>
Line 57, Delete "PREFERED" and insert --PREFERRED-- therefore.

<u>Column 5</u>
Line 37, delete "densificaiton" and insert --densification-- therefore.

<u>Column 6</u>
Line 45, delete "for" and insert --For-- therefore.

<u>Column 10</u>
Line 32, in claim 13, after "method" insert --of--.

Signed and Sealed this
Fifth Day of April, 2011

David J. Kappos
*Director of the United States Patent and Trademark Office*